United States Patent [19]

Yabe

[11] Patent Number: 4,562,830
[45] Date of Patent: Jan. 7, 1986

[54] SUCTION DEVICE FOR AN ENDOSCOPE
[75] Inventor: Hisao Yabe, Tokyo, Japan
[73] Assignee: Olympus Optical Co., Ltd., Tokyo, Japan
[21] Appl. No.: 685,618
[22] Filed: Dec. 28, 1984

Related U.S. Application Data

[63] Continuation of Ser. No. 415,977, Sep. 8, 1982, abandoned.

[30] Foreign Application Priority Data

Sep. 17, 1981 [JP] Japan .................................. 56-146523
Sep. 26, 1981 [JP] Japan .................................. 56-152689

[51] Int. Cl.$^4$ ............................................... A61B 1/00
[52] U.S. Cl. ........................................................ 128/4
[58] Field of Search ......................................... 128/4-8; 251/320

[56] References Cited

U.S. PATENT DOCUMENTS 2,657,563 11/1953 Burchett .............................. 251/320
3,726,272 4/1973 Fukami et al. ......................... 128/6
3,958,566 5/1976 Furihata ................................ 128/4
4,270,525 6/1981 Furihata ................................ 128/4
4,325,362 4/1983 Ouchi et al. .......................... 128/4

Primary Examiner—Edward M. Coven
Assistant Examiner—Max F. Hindenburg

[57] ABSTRACT

A suction device comprises a suction changeover valve provided to a control section of an endoscope and including a cylinder with an opening at one end and a closed wall at the other end, and a piston held in the cylinder in a state movable therethrough and removable through the opening of the cylinder, a first suction tube section formed in the insertion section in a state communicable with the cylinder through the closed wall; and a second tube section formed in a cord of the endoscope in a state communicable with the cylinder through the closed wall. An urging member is projectively provided to the control section, shaped like a cup to cover the opening of the cylinder, and engaged with one end of the piston to elastically hold the piston in the first position.

6 Claims, 8 Drawing Figures

SUCTION DEVICE FOR AN ENDOSCOPE

This application is a continuation of application Ser. No. 415,977, filed Sept. 8, 1982, abandoned 3/1/85.

BACKGROUND OF THE INVENTION

This invention relates to a suction device for an endoscope allowing for easy brushing of the interior of a suction pipe.

An endoscope is generally provided with a suction tube, through which, for example, a viscous liquid, filth and blood retained in the coeliac cavity are drawn off. This suction tube is generally divided into a first section constituting the upstream region extending from the control section of the endoscope to the tip of the distal end of the insertion section and a second section constituting the downstream region extending from said control section to the connector connected to the end of the universal cord.

Those portions of the first and second tube sections which are held in the control section are partly connected to a suction changeover valve provided in the control section. Operation of said suction changeover valve effects suction.

Recently, problems have arisen because of a hospital infection resulting from HB antigens. To avoid the occurrence of such event, it is strongly recommended not only to pass a disinfecting liquid through a suction tube generally contaminated by patient's blood, but also to force a brush into the suction tube to clean its interior. To this end, it is contemplated to detachably fit a piston constituting the suction changeover valve into a cylinder and, when the piston is removed, to insert a brush from a cylinder open at the control section into the upstream region of the suction tube partly connected to the cylinder there to clean the interior of said upstream region. When, however, a brush is inserted into a suction tube at the other end of the first tube region open to the distal end of the insertion section or at the other end of the second tube region open to the connector, then the filth remaining in the suction tube tends to leak from the suction changeover valve to the control section. If the angle knob and eyepiece provided in the control section are contaminated, then much effort will be needed to wash and disinfect these members. When, therefore, the suction tube is to be brushed, it is preferable to insert a brush from the cylinder holding the detachable suction changeover valve into both upstream and downstream tube regions.

With the conventional endoscope, however, either upstream or downstream region the suction tube is connected at one end to the peripheral wall of the cylinder. Therefore, one end of that suction tube region which is connected to the peripheral wall of the cylinder is open in a direction intersecting the axis of the cylinder at right angles. Consequently considerable difficulties are encountered in inserting a brush into said suction tube region. If it is tried to forcefully pass a brush through said suction tube region, the brush will be damaged at once.

SUMMARY OF THE INVENTION

It is accordingly the object of this invention to provide a suction device for an endoscope, wherein the upstream and downstream regions of a suction tube are connected at one end to the bottom of a cylinder, thereby allowing for the easy insertion without damage of a brush into said upstream and downstream suction tube regions for efficient cleaning.

BRIEF DESCRIPTION OF THE DRAWINGS

FIGS. 1 to 4 show a suction device for an endoscope according to one embodiment of this invention, wherein FIG. 1 is a schematic view of the whole endoscope, FIGS. 2 and 3 are sectional views of the suction device, showing its different operating conditions and FIG. 4 is a sectional view showing the condition in which the suction tube is brushed with the suction changeover valve taken off.

DETAILED DESCRIPTION OF THE PREFERRED EMBODIMENTS

Figure 1:
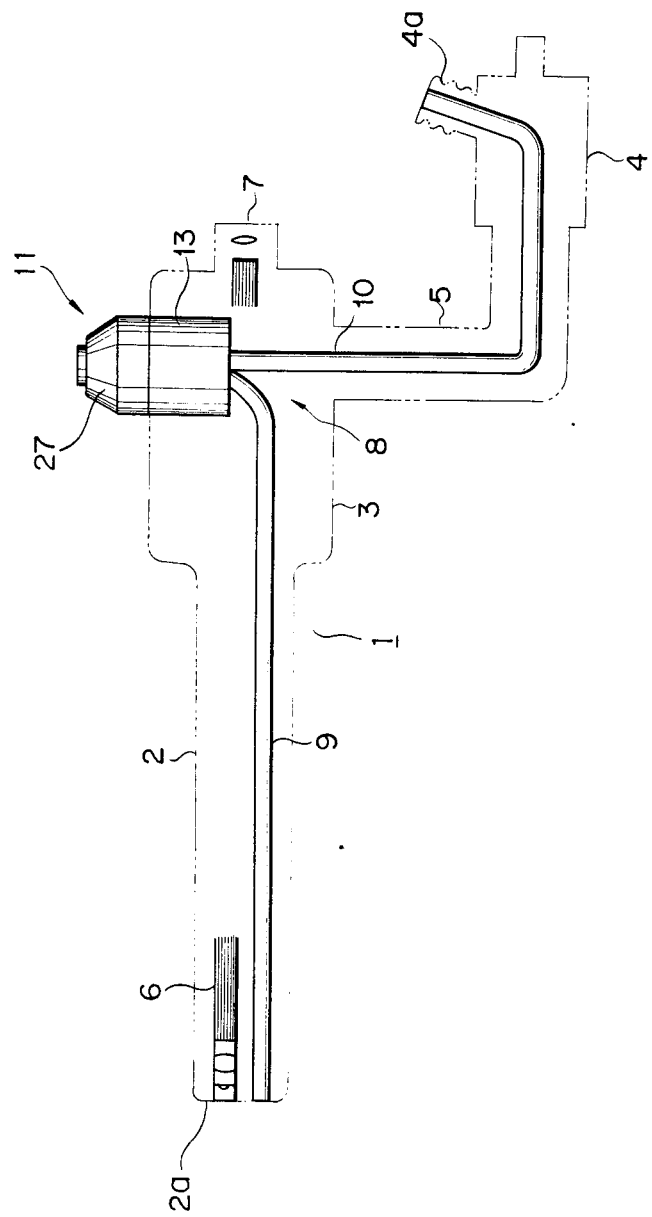

Description is now given with reference to FIGS. 1 to 4 of a suction device for an endoscope according to one embodiment of this invention. Reference numeral 1 denotes an endoscope including an insertion section 2 introduced into the coeliac cavity of the human body, and a control section 3 set outside of the human body. The control section 3 is connected to a universal cord 5 whose end is fitted with a connector 4. The outer end of the insertion section 2 is provided with an observation optical system 6, which is optically connected to an eyepiece section 7.

A suction tube 8 extends through the endoscope 1. This suction tube 8 comprises a first suction tube section 9 constituting an upstream region extending from the distal end of the insertion section 2 to the control section 3 and a second suction tube section 10 constituting a downstream region extending from the control section 3 to the connector 4 through the universal cord 5. The first suction tube section 9 is connected at one end to a suction changeover valve 11 provided in the control section 3 and at the other end is open to the distal end 2a of the insert section 2. The second suction tube section 10 is connected at one end to the suction changeover valve 11 and at the other end communicates with a mouthpiece 4a connected to a suction pump (not shown) fitted to the connector 4.

Figure 2:
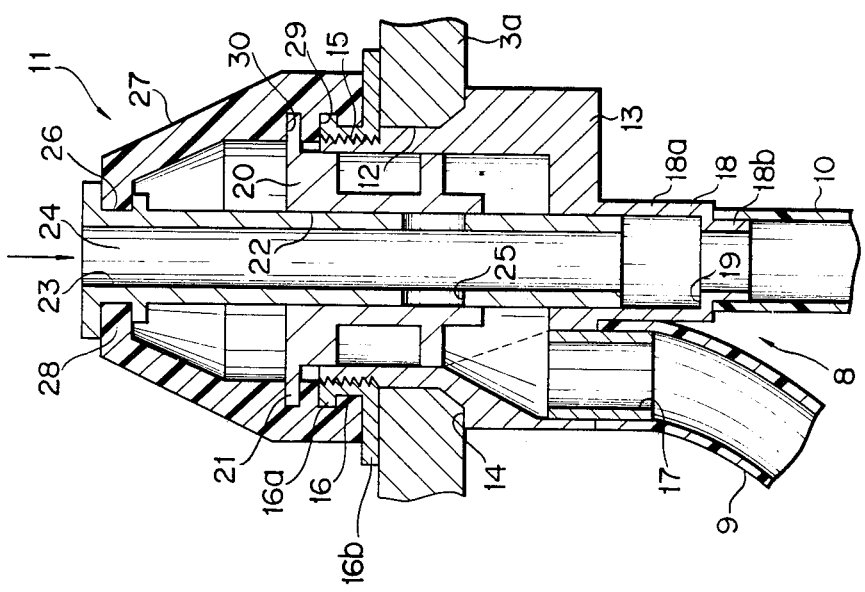
Figure 3:
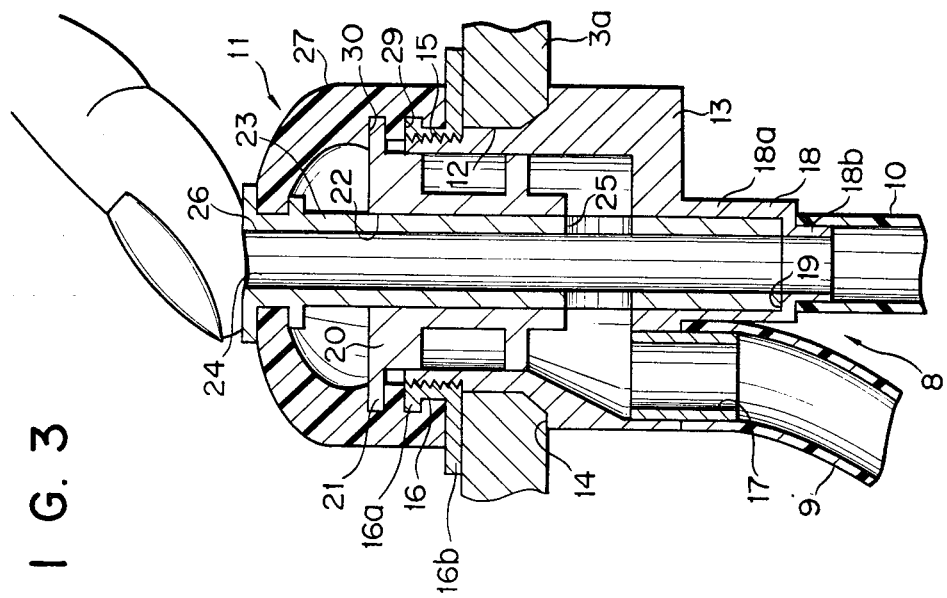

The suction changeover valve 11 is constructed as shown in FIGS. 2 and 3. The outer wall 3a of the control section 3 has a fitting hole 12 drilled into it, into which a first cylinder 13 is inserted. The upper portion of the first cylinder 13 projects to the outside of the control section 3 through its outer wall 3a. Said projecting upper portion of the first cylinder 13 is shaped like a blind cylinder open at the projecting end. A stepped portion 14 engageable with the inside of the outer peripheral wall 3a of the control section 3 is formed in the intermediate part of said cylinder 13. A male screw 15 in formed is the outer wall of cylinder 13. A female screw formed in the inner wall of an annular stop member 16 is engaged with said male screw 15. The first cylinder 13 is fixed to the outer wall 3a of the control section 3 by means of the annular stop member 16 whose lower end portion is pressed against said outer wall 3a and the stepped portion 14. The annular fitting member 16 comprises an upper flange 16a and a lower flange 16b having a larger diameter than said upper flange 16a and has a cross section substantially shaped like a trough. The bottom of the lower flange 16b is pressed against said outer wall 3a. Provided at the bottom of the first cylinder 13 are a first connection tube 17 eccentrically set from the axis of the first cylinder 13 and a second connection tube 18 set concentric with said axis. The second connection tube 18 includes a larger diameter section 18a closely facing the first cylinder 13 and a smaller diameter section 18b remote from said first cylinder 13. A stepped portion 19 is formed at the boundary between said larger diameter section 18a and smaller diameter section 18b. The first connection tube is connected to one end of the first suction tube section 9. The smaller diameter section 18b of the second connection tube 18 is connected to one end of the second suction tube section 10. The first and second suction tube sections 9, 10 are so arranged that they are open at one end to the bottom of the first cylinder. A second cylinder 20 is concentrically inserted into the first cylinder 13. The outer peripheral wall of the second cylinder 20 is pressed against the inner peripheral wall of the first cylinder 13. The upper end portion of said second cylinder 20 which projects from the first cylinder is fitted with a flange 21 having substantially the same diameter as the flange 16a of the fitting member 16. The aforementioned end portion is penetrated by a concentric passage 22. A piston 23 is inserted into said passage 22 in a vertically slidable state. A leak path 24 axially extends throughout the hollow piston 23 in a state open at both upper and lower ends. A pair of mutually facing holes 25 are formed in the intermediate part of the peripheral wall of the leak path 24 for communication therewith. The hollow piston 23 further comprises a pair of annular flanges formed on the outer peripheral wall of the upper end portion projecting out of the second cylinder 20. Said paired flanges are vertically spaced from each other to define an annular depression 26 therebetween. The hollow piston 23 is elastically supported by an urging member 27 prepared from an elastic material such as synthetic resin or rubber in such a manner that the upper portion of said hollow piston 23 can project out of the second cylinder 20. The urging member 27 is shaped like a skirt open at both upper and lower ends. The upper end portion of said urging member 27 is fitted with an annular flange 28 which projects diametrically inward. Formed in the lower inner peripheral wall of said urging member 27 are a first annular groove 29 and a second annular groove 30 in a state vertically spaced from each other. The first and second annular grooves 29, 30 are respectively and detachably engaged with the upper flange 16a of the fitting member 16 and the flange 21 of the second cylinder 20. The annular flange 28 is engaged with the depression 26 of the hollow piston 23. The urging member 27 surrounds the outer peripheral wall of the upper portion of the piston 23 in the above-mentioned condition. When the first annular groove 29 of the urging member 27 is disengaged from the upper flange 16a of the fitting member 16, then said urging member 27, hollow piston 23 and second cylinder 20 can be removed together from the first cylinder 13.

When the hollow piston 23 is held in an upper position by the urging member 27 as shown in FIG. 2, then the communication hole 25 formed in the hollow piston 23 is brought into the passage 22 and closed by the inner peripheral wall of the second cylinder. At this time, the lower portion of suction tube section 10 is fitted into the second connection tube 18, causing the first suction tube section 9 and second suction tube section 10 to be shut off. When the holllow piston 23 is pressed downward against the righting moment of the urging member 27, until its lower end face touches the stepped section formed in the second connection tube 18, then the communication hole 25 is exposed from the passage 22 of the second cylinder 20, causing the first suction tube section 9 and second suction tube section 10 to communicate with each other through said communication hole 25.

With an endoscope arranged as described above, let it be assumed that a suction pump (not shown) connected to the mouthpiece 4a of the connector 4 is put into operation. If, in this case, the suction changeover valve 11 is not actuated as indicated in FIG. 2, then the first suction tube section 9 and second suction tube section 10 are shut off by the hollow piston 23. Therefore, atmospheric air is taken in through the leak path 24 of the hollow piston 23 by a suction force acting on the second suction tube section 10. Consequently, for example, filthy substances remaining in the coeliac cavity are prevented from being sucked up. The removal of the filthy substances in the coeliac cavity is effected by the following process. First, the hollow piston 23 is pressed downward with the leak path 24 closed by the finger as illustrated in FIG. 3. At this time the first suction tube section 9 and second suction tube section 10 communicate with each other through the penetrating holes provided outside 25 of the hollow piston 23. As a result, a suction force is applied to the first suction tube section 9 through the second suction tube section 10, thereby effecting the removal of, for example, filthy substances remaining in the coeliac cavity.

Figure 4:
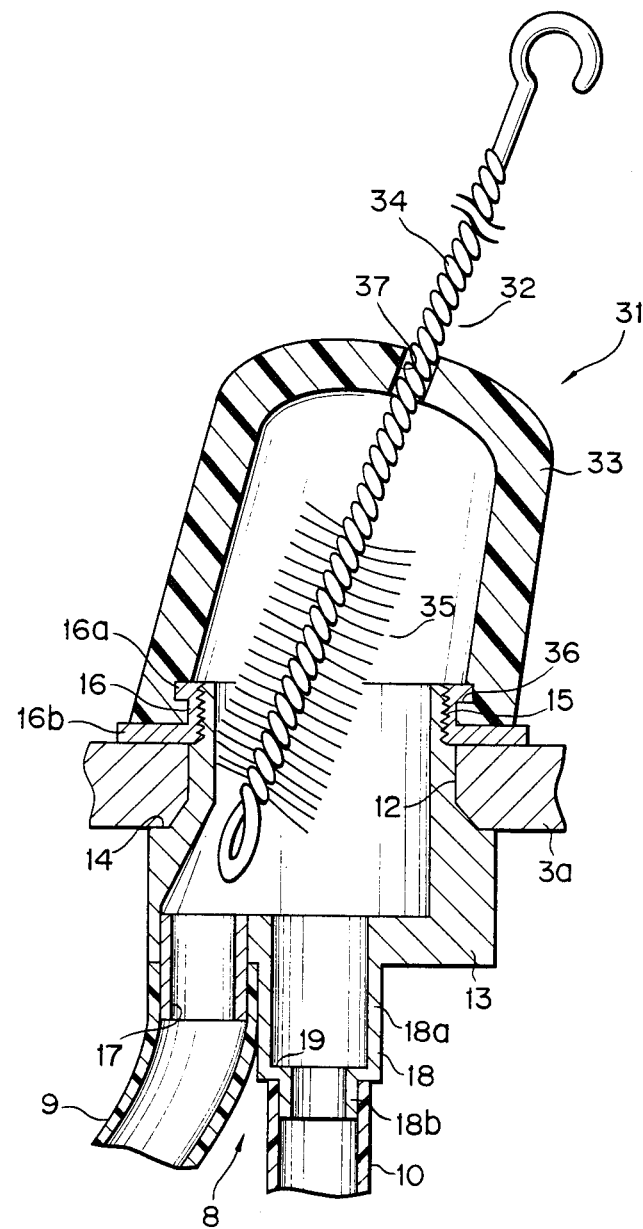

With the endoscope thus applied, the suction tube 8 is contaminated by, for example, filthy substances, and has to be washed after said application. In this case, a washing device 31 illustrated in FIG. 4 is used. This washing device 31 comprises a brush 32 and a cover 33 prepared from a transparent elastic material such as flexible synthetic resin or rubber. The brush 32 comprises a hairy section 35 which is constructed by planting a large number of brush hairs of the prescribed length in the leading end portion of an assembly of twisted wires 34. The transparent cover 33 is shaped like a cap open at the bottom. A fitting groove 36 detachably engaged with the upper flange 16a of the fitting member 16 is formed in the inner peripheral wall of the lower portion of the transparent cover 33. A penetrating hole 37 is drilled in the top of the transparent cover 33. The assembly of twisted wires 34 passes through said penetrating hole 37 in a substantially airtight state. The transparent cover 33 is chosen to have such a height that when the cover 33 is set on the fitting member 16 as later described, a height of a sum of a space defined in the transparent cover 33 and a space defined in the first cylinder 13 has a greater height than the length of the hairy section 35 of the brush 32.

The suction tube 8 is washed by the washing device 3 in the following manner. First, a sufficient amount of a disinfecting liquid is fully taken into the suction tube 8 by the ordinary suction process. Air is drawn in to remove water deposited on the inner wall of the suction tube 8, and the suction pump (not shown) is brought to rest. The urging member 27, hollow piston 23 and second cylinder 20 are taken off the first cylinder 13. Thereafter, the transparent cover 33 into which the brush 32 has been inserted is fitted to the opening of the first cylinder 13, that is, the upper flange 16a of the fitting member 16 with the fitting groove 36 is engaged therewith. Thereafter, the brush 32 is first inserted into the first suction tube section 9 through the first connection tube 17, until the haired section 35 protrudes from the distal end 2a of the insertion section 2 to be dipped in a disinfecting liquid. At this time, the suction pump is again actuated. The brush is pulled while sucking the disinfecting liquid. The inner wall of the first suction tube section 9 is disinfected while being brushed. At this time, the first cylinder 13 is fitted with the cover 33, and the wire assembly 34 of the brush 32 is inserted into the penetrating hole 37 of the cover 33 in a substantially airtight state. Therefore, a disinfecting liquid or filthy substances are prevented from being scattered to the outside. The interior of the first suction tube section 9 is brushed while looking through the transparent cover 33 at the color of the disinfecting liquid flowing through the first cylinder 13.

After the brushing of the interior of the first suction tube section 9 is brought to an end, the hairy section 35 of the brush 32 is pulled out of said first suction tube section 9, and then taken into the second suction tube section 10. Since the hairy section 35 of the brush 32 is shorter than the height of a sum of a space defined in the first cylinder 13 and a space defined in the cover 33, the hairy section 35 of the brush 32 can be shifted from the first suction tube section 9 to the second suction tube section 10 without taking off the cover 33, thereby rendering said operation quite sanitary for the operator. Thereafter, the brush 32 is inserted into the second suction tube section 10 for brushing while letting the disinfecting liquid run through said section 10 as in the case of the first suction tube section 9. If the mouthpiece 4a of the connector 4 and suction pump (not shown) are connected by a transparent hose at the brushing of the second suction tube section 10, then it is possible to recognize whether the hairy section 35 of the brush 32 has protruded from the mouthpiece 4a when the brush 32 is inserted into the second suction tube section 10, and also to observe the color of a disinfecting liquid flowing through the second suction tube section 10.

With the suction changeover valve 11 arranged as described above, the first and second suction tube sections 9, 10 are open at one end to the bottom of the first cylinder 13. Therefore, the brush 32 can be easily inserted from the first cylinder 13 into the first and second suction tube sections 9, 10 without bending the leading end portion of the brush 32. When the suction tube 8 is brushed without applying the cover 33, it is advised to carry out only brushing by stopping the suction pump and without running a disinfecting liquid.

Description is now given with reference to FIGS. 5 to 8 of endoscope suction devices according to the second to the fifth embodiments of this invention. The suction changeover valve 11 used with these second to the fifth embodiments has a different arrangement from that of the first embodiment.

Figure 5:
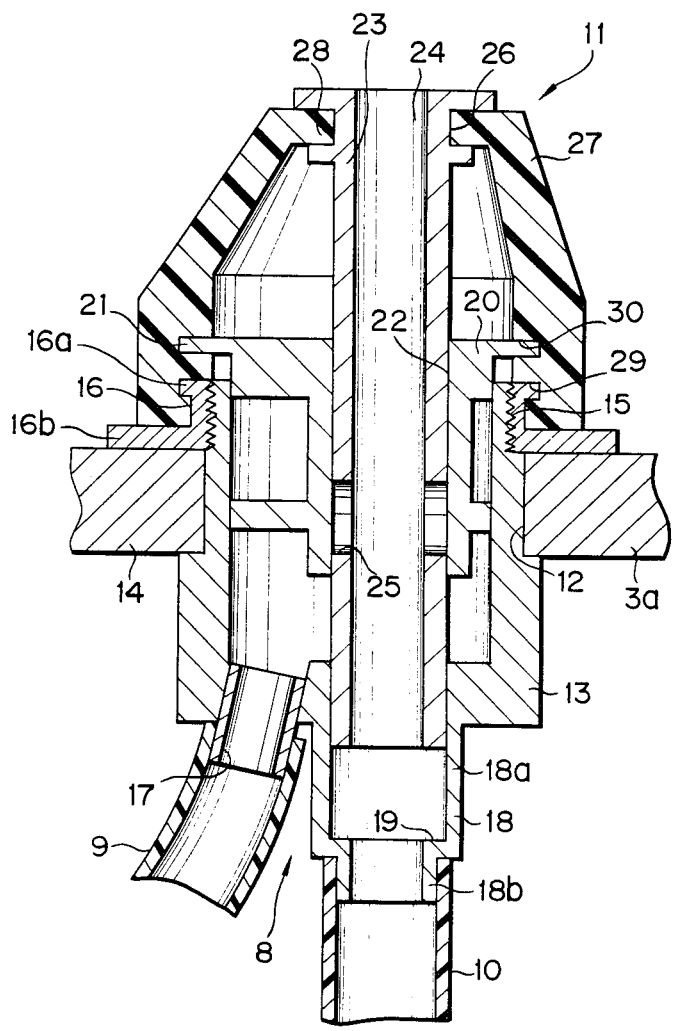
FIGS. 5 to 8 are sectional views of suction devices according to other embodiments of the invention.

In the second embodiment of FIG. 5, a penetrating hole 22 eccentrically extends through the second cylinder 20 into which the hollow piston 23 is inserted. The annular flange 28 formed on the urging member 27 to hold the hollow piston 23 is also eccentrically set to match the passage 22. The second connection tube 18 to which one end of the second suction tube section 10 is connected also assumes an eccentric position corresponding to the hollow piston 23 held at the bottom of the first cylinder 13. The first connection tube 17 to which one end of the first suction tube section is connected to the bottom of the first cylinder 13 in a state inclined to its axis.

As described above, the second connection tube 18 is eccentrically connected to the bottom of the first cylinder 13. Therefore, the first connection tube 17 can be connected in a state more displaced toward the axis of the bottom of the first cylinder 13 than in the first embodiment, thereby allowing for easy insertion of the brush 32 from the first connection tube 17 into the first suction tube section 9. Further, the inclination of the first connection tube 17 assures the easy insertion of the brush 32.

Figure 6:
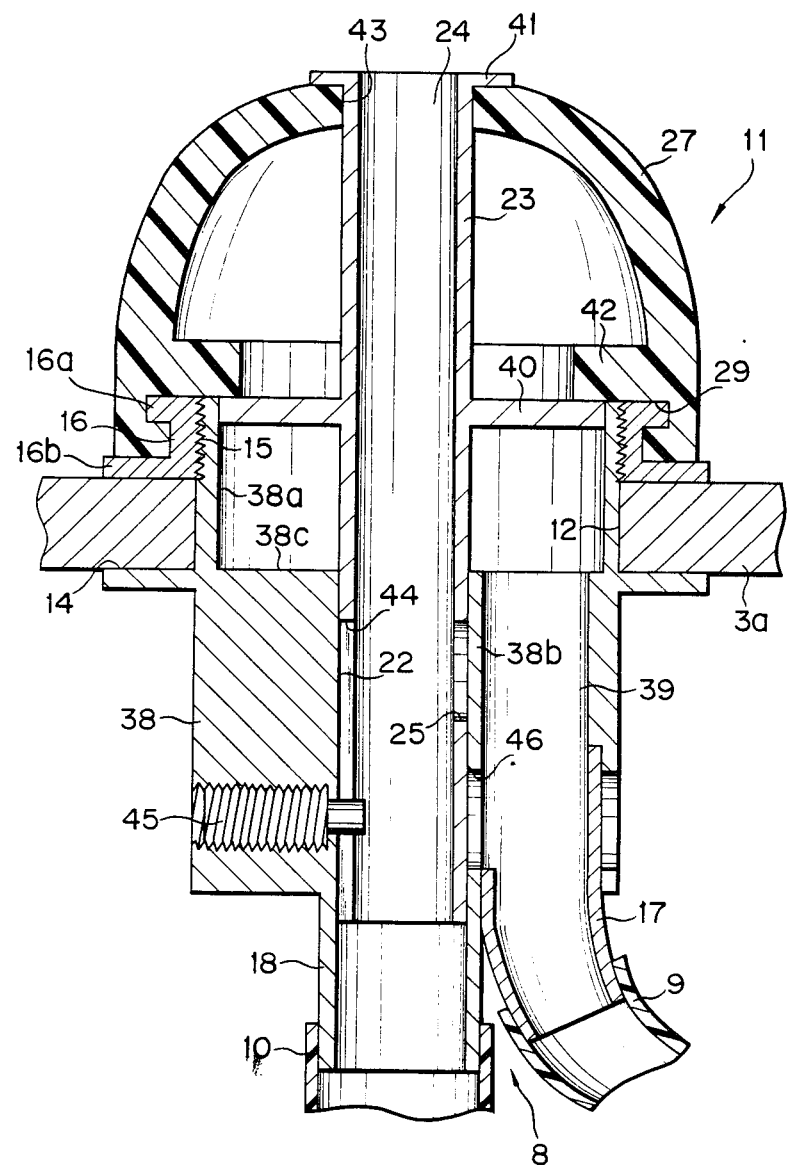

Referring to the third embodiment of FIG. 6, a larger diameter circular depression 38a is formed in the upper surface of the cylinder 38. The passage 22 and the upper end of a brush hole 39 are open to the bottom plane of said depression 38a. The passage 22 extends parallel with the axis of the cylinder 38. The brush hole 39 is partitioned by means of the passage 22 and wall 38b, and extends parallel with said passage 22. The passage 22 and brush hole 39 respectively communicate at the lower end with the connection tubes 18, 17. A cylinder depression 38a is formed in the intermediate part of the piston 23. A first flange 40 having substantially the same diameter as that of said cylinder depression 38a is set therein. A second flange 41 having a smaller diameter than said first flange 40 is provided at the upper end of the hollow piston 23. The urging member elastically supporting the hollow piston 23 has a substantially semispherical form. Provided on the inner peripheral wall of the bottom of said urging member 27 are a first annular groove 29 detachably engaged with the upper flange 16a of the stop member 16 and a ridge 42 projecting diametrically inward from the upper opening of the cylinder 38. The center of the top of the semispherical urging member 27 is provided with an engagement hole 43 having a diameter substantially the same as the outer diameter of the piston 23. The hollow piston 23 is elastically held by the second flange 41 engaged with the outer peripheral wall of the semispherical urging member 27 provided with the aforesaid engagement hole 43. Further, the hollow piston 23 is prevented from being pulled out of the cylinder 38, because the upper peripheral surface of the first flange 40 fitted into the depression 38a of the cylinder 38 is engaged with the underside of the aforementioned ridge 42. The lower part of the hollow piston 23 is provided with a rotation-preventing groove 44 which extends along said hollow piston 23 and is open to the bottom thereof. The outer end of a locating pin 45 threaded into the cylinder 38 is engaged with said rotation-preventing groove 44 to prevent the rotation of the hollow piston 23. The partition wall 38b separating the passage 22 from the brush hole 39 is provided with a crosswise extending hole 46. This crosswise extending hole 46 normally is in a lower position. When the hollow piston 23 is inserted until the first flange 40 of said piston 23 is pressed against the bottom 38c of a depression formed in the cylinder 38, then said crosswise extending hole 46 faces the communication hole 25, causing the first suction tube section 9 and second suction tube section 10 to communicate with each other. Also with the above-mentioned arrangement, it is possible to clean the interior of the first suction tube section 9 by inserting the brush 32 through the brush hole 39 and to clean the interior of the second suction tube section 10 by inserting the brush 32 through the passage 22.

Figure 7:
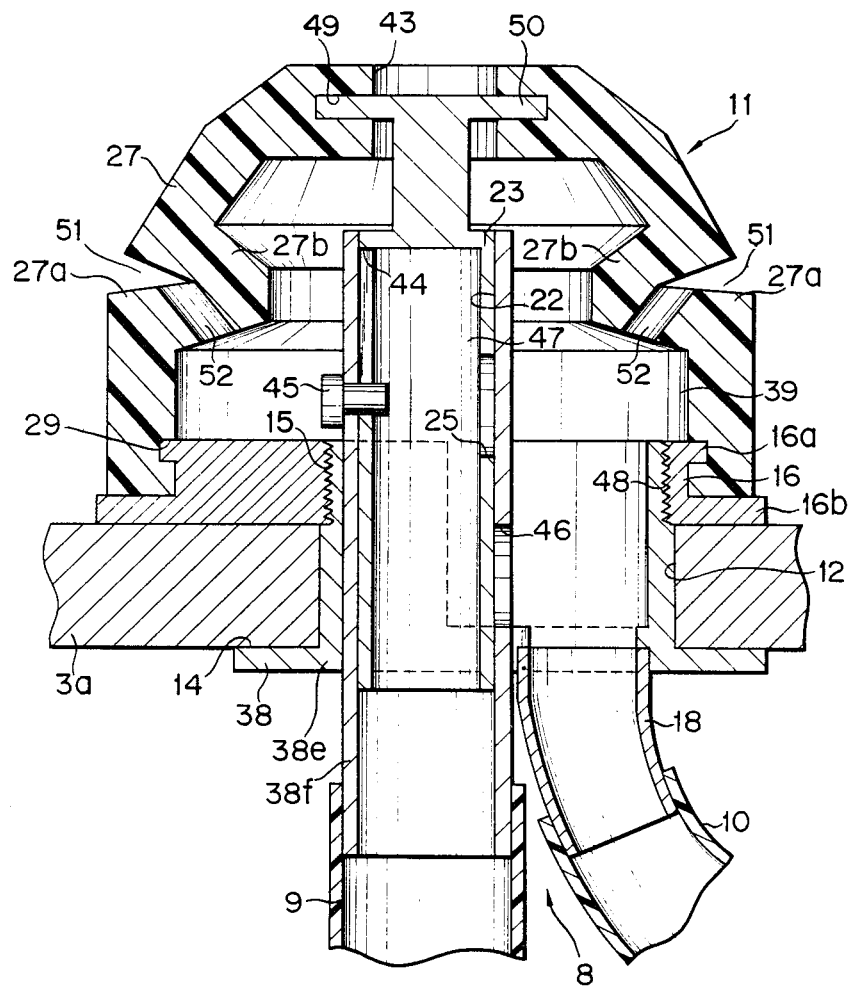

Description is now given with reference to FIG. 7 of an endoscope suction device according to a fourth embodiment of this invention. Like the third embodiment, the endoscope suction device of FIG. 7 comprises a cylinder 38 but is slightly different from said third embodiment in the construction of various parts. The cylinder 38 consists of a larger diameter cylinder 38e whose lower end is provided with a flange and a smaller diameter cylinder 38f. Both larger and smaller diameter cylinders 38e, 38f are integrally secured in place. The smaller diameter cylinder 38f eccentrically extends through the larger diameter cylinder 38e. The smaller diameter cylinder 38f defines the passage 22 through which the piston 23 reciprocates. The lower end portion of the larger diameter cylinder 38e concurrently constitutes a first connection tube to which the first suction tube section 9 is connected. A space defined between the inner peripheral wall of the larger diameter cylinder 38e and the outer peripheral wall of the smaller diameter cylinder 38f constitutes a brush hole 39. A second connection tube 18 to which the second suction tube section 10 is connected is attached to the bottom of the larger diameter cylinder 38e in a state outwardly inclined to the axis thereof. The hollow piston 23 assumes a cylindrical form whose upper end is closed and whose lower end is open. The interior space of said hollow piston 23 constitutes a passage 47. The hollow piston 23 is not provided with a leak path directly open to the atmosphere. The upper peripheral wall of the hollow piston 23 is provided with an axially extending rotation-preventing slot 44. A rotation-preventing pin 45 fitted to the peripheral wall of the smaller diameter cylinder 38f is engaged with said slot 44, thereby suppressing the rotation of the piston 23.

The fitting member for inserting the larger and smaller diameter cylinders 38e, 38f into a fitting hole 12 drilled in the wall 3a of the control section 3 of the endoscope is provided with a screw hole 48 into which said larger and smaller diameter cylinders 38e, 38f are threadedly inserted. Said screw hole 48 is formed eccentrically with the hollow piston 23 to face the larger diameter cylinder 38e. The urging member 27 is constructed by causing the first annular groove 29 formed in the lower inner peripheral wall of said urging member 27 to be engaged with the upper flange 16a of the fitting member 16. This urging member 27 is mounted on a rotor aligned with the axis thereof. An annular groove 49 is formed in the inner peripheral wall of an engagement hole 43 drilled in the top of said urging member 27. A flange 50 provided at the upper end of the hollow piston 23 is engaged with said annular groove 49. An inward extending constricted portion 51 is formed in the outer peripheral wall of the urging member 27. A suction hole 52 is formed in one wall 27a of said constricted portion 51 to effect communication between the urging member 27 and the outside. While the hollow piston 23 is elastically held by the urging member 27 as illustrated in FIG. 7, the communication hole 25 formed in the hollow piston 23 and the hole 46 formed crosswise to the wall of the smaller diameter cylinder 38f are both shut off. Consequently, air is drawn in by a suction force generated in the second suction tube section 10 through the brush hole 39 and also the suction hole 52 drilled in the urging member 27. When the hollow piston 23 is inserted, the first and second suction tube section 9, 10 communicate with each other through the communication hole 25 and the hole extending through the wall of the smaller diameter cylinder 38f. At this time, the urging member 27 is compressed to cause one wall 27a of the constricted portion 51 to be tightly pressed against the other wall 27b thereof, thereby tightly closing the suction hole 52. As a result, a suction force generated in the second suction tube section 10 acts on the first suction tube section 9 to draw off filthy substancs in the coeliac cavity of a patient.

Like the preceding embodiments, the fourth embodiment of FIG. 7 arranged as described above enables the interior of the first and second suction tube sections 9, 10 to be cleaned by inserting a brush 32 therethrough. Further, the passage 22 and second connection tube 18 are inclined to facilitate the insertion of the brush 32 through the first and second suction tube sections 9, 10 as in the second embodiment of FIG. 5.

Figure 8:
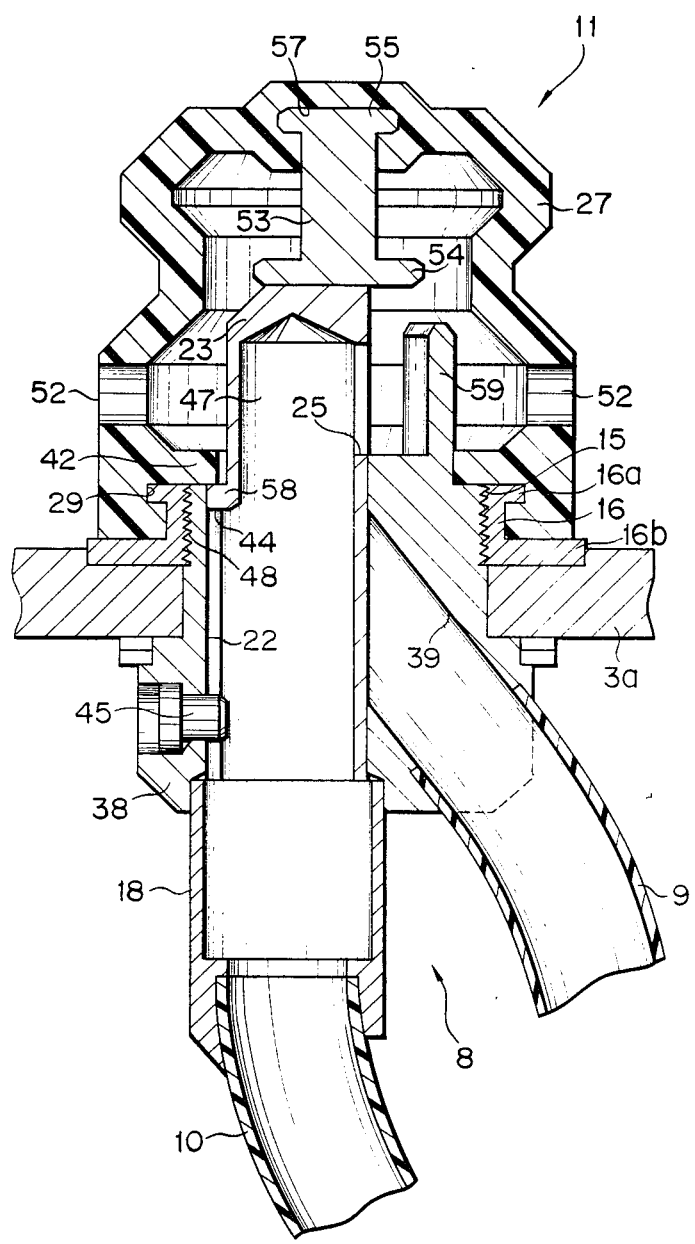

Description is now given with reference to FIG. 8 of an endoscope suction device according to a fifth embodiment of this invention. The suction changeover valve 11 of this fifth embodiment has a construction resulting from a combination of the arrangements of the suction changeover valves of the third embodiment of FIG. 6 and the fourth embodiment of FIG. 7. The passage 22 is drilled eccentrically to the cylinder 38. The second connection tube 18 to which the second suction tube section 10 is fitted to the lower end of said passage 22, namely, the bottom of the cylinder 38. This cylinder 38 is provided with a brush hole 39 which is inclined to the axis of said cylinder 38, one end of which communicates with the passage 22 and the other end of which is open to the bottom of the cylinder 38. The first suction tube section 9 is directly connected to said brush hole 39.

The hollow piston 23 inserted into the passage 22 has a cylindrical form whose upper end is closed, and whose lower end is open. The interior space of said hollow piston 23 is used as a communication path 47. The hollow piston 23 is not provided with a leak path directly open to the atmosphere. A rotation-preventing slot 44 is provided which is open to the bottom of the hollow piston 23. The outer end of a rotation preventing pin 45 extending diametrically to the cylinder 38 is engaged with said rotation-preventing slot 44, thereby preventing the rotation of the hollow piston 23. Connected to the upper end of the hollow piston 23 is a shaft 53 which is set eccentric from said hollow piston 23, but concentric with the cylinder 38. A first flange 54 is provided at the lower end of said shaft 53, and a second flange 55 is formed at the upper end of said shaft 53. The cross section of the peripheral wall of an urging member 27 elastically holding the hollow piston 23 has a zigzag outline. A suction hole 52 is drilled in one of the convex portions of said zigzag peripheral wall of the urging member 27. A depression 57 is formed in the inner wall of the top portion of the urging member 27 for engagement with the second flange 55 of the shaft 53. Provided in the inner peripheral wall of the lower end of the urging member 27 is a ridge 42 which is engaged with the upper and lower planes of a projection 58 formed on the intermediate part of the outer peripheral wall of the piston 23.

While the hollow piston 23 is held in a lifted position by the urging member 27 as illustrated in FIG. 8, the communication hole 25 formed in the wall of the hollow piston 23 is made to communicate with the atmosphere at the upper end of the cylinder 38. As a result, the second suction tube section 10 can communicate with the atmosphere through said communication hole 25 and the suction hole 52 formed in the urging member 27. A brush hole 39 is closed by that portion of the piston 23 which is received in the passage 22. A projecting wall block 59 is provided at the upper end portion of the cylinder 38 at a point facing the communication hole 25. This wall block 59 prevents filthy substances carried through the communication path 47 from being ejected from the suction hole 52 through the communication hole 25.

When the hollow piston 23 is pressed downward against the righting moment of the urging member 27 until the first flange 54 formed at the lower end of the shaft 53 is pressed against the upper end of the cylinder 38, then the communication hole 25 is made to face the brush hole 39, thereby causing the first and second suction tube sections 9, 10 to communicate with each other through the communication hole 47 formed in the piston 23.

An endoscope suction device arranged as described with reference to FIG. 8 also enables the interior of the first and second suction tube sections 9, 10 to be cleaned by inserting the brush 32 therethrough when both urging member 27 and piston 23 are taken off the cylinder 38.

With an endoscope suction device embodying this invention, the upstream and downstream sections are connected at one end, as previously described, to the bottom of the suction changeover cylinder. Therefore, the brush 32 can be inserted into the upstream and downstream sections of the suction tube from the cylinder without being damaged, thereby assuring the reliable and efficient brushing of the suction tube.

What is claimed is:

1. A suction device for an endoscope, which endoscope includes an insertion section, a control section connected to one end of said insertion section and a cord extending from the control section to the outside, comprising;

a suction changeover valve provided on the control section and including a cylinder with a longitudinal passage having a longitudinal axis and a downwardly inclined passage disposed at an angle of less than ninety degrees to said longitudinal axis of said longitudinal passage and intersecting said longitudinal passage, an opening at one end of said passage, said cylinder having a bottom wall and a peripheral wall, said bottom wall having first and second holes adjacent to each other, and a piston held in said longitudinal passage and removable axially through said opening thereof;

a first suction tube section extending through the insertion section to communicate with said inclined passage through the first hole of the bottom wall; and a second suction tube section extending through the cord to communicate with said longitudinal passage through the second hole of the bottom wall, whereby a linear cleaning instrument can be inserted through said inclined and longitudinal passages into said first and second holes and first and second suction tube sections without significant deflection of that instrument from a linear configuration when said piston is removed from said longitudinal passage.

2. The suction device according to claim 1, wherein said piston includes a peripheral wall defining a communication path extending along a longitudinal axis thereof and communicated with said second suction tube section at one end of said piston, and a communication hole formed in the peripheral wall of the piston to communicate with the communication path, the piston being provided in the cylinder to be movable between a first position where the communication hole is communicated with the atmosphere, and a second position where the first suction tube section is communicated with the second suction tube section through the communication path and the communication hole.

3. The suction device according to claim 2, which further includes an urging member which projects from the control section and is engaged with one end of the piston to elastically hold the piston in the first position.

4. The suction device according to claim 3, wherein said urging member is deformable between an extended position where the piston is kept in the first position and a depressed position where the piston is moved into the second position.

5. The suction device according to claim 2, wherein said second suction tube section is provided in coaxial relation with the piston to always communicate therewith at its end, and said communication hole communicates the second suction tube section to the atmosphere when the piston is located in the first position.

6. The suction device according to claim 2, in which said cylinder is fixed to the control section, and at least one of the first and second suction tube sections includes a connection tube eccentrically opened into the cylinder in the bottom wall of the cylinder.

* * * * *